United States Patent [19]
Taguchi et al.

[11] Patent Number: 5,115,142
[45] Date of Patent: May 19, 1992

[54] DEVICE FOR DETECTING EDGE OF TRANSPARENT SHEET OF LAMINATED TRANSPARENT AND TRANSLUCENT SHEET ASSEMBLY

[75] Inventors: Chiaki Taguchi, Hisai; Hiroyuki Nishii, Ise, both of Japan

[73] Assignee: Central Glass Company, Limited, Ube, Japan

[21] Appl. No.: 567,906

[22] Filed: Aug. 15, 1990

[30] Foreign Application Priority Data

Aug. 18, 1989 [JP] Japan .................................. 1-212438
Aug. 18, 1989 [JP] Japan .................................. 1-212439

[51] Int. Cl.$^5$ ............................................ G01N 21/86
[52] U.S. Cl. ................................... 250/561; 250/548
[58] Field of Search ...................... 250/548, 557, 561; 83/879; 356/375; 364/473, 474.03, 474.32, 474.33, 474.36

[56] References Cited

U.S. PATENT DOCUMENTS

| | | | |
|---|---|---|---|
| 4,238,780 | 12/1980 | Doemens | 250/561 |
| 4,564,912 | 1/1986 | Schwefel | 364/474.32 |
| 4,680,719 | 7/1987 | Kishi et al. | 364/474.32 |

*Primary Examiner*—David C. Nelms
*Attorney, Agent, or Firm*—Fleit, Jacobson, Cohn, Price, Holman & Stern

[57] ABSTRACT

A device for detecting an edge of a transparent sheet of a laminated transparent and translucent sheet assembly, is provided which includes a light source for producing a shadow of the edge of the transparent sheet on a translucent sheet, a photosensor operative to produce an electrical output which varies depending upon variation of intensity of light supplied thereto, and a lens for producing a clear image of the shadow on the photosensor. A picture processing unit determines the position of the edge of the transparent sheet on the basis of a variation of the output of the photosensor.

12 Claims, 3 Drawing Sheets

DEVICE FOR DETECTING EDGE OF TRANSPARENT SHEET OF LAMINATED TRANSPARENT AND TRANSLUCENT SHEET ASSEMBLY

BACKGROUND OF THE INVENTION

1. Field of the Invention

The present invention relates to a device for detecting an edge of a transparent sheet of a laminated transparent and translucent sheet assembly as an assembly of two transparent glass sheets between which a translucent interlayer is sandwiched. The present invention further relates to laminated safety glass for an automobile windshield, etc. and to an apparatus for cutting off, in production of laminated safety glass, a protruding end portion of an interlayer sandwiched between two glass sheets.

2. Description of the Prior Art

Generally, an automobile windshield is formed from laminated safety glass which consists of two glass sheets and an interlayer of polyvinyl butyral or the like sandwiched between the glass sheets and bonded to same.

In production of laminated safety glass, the interlayer is first sized a little larger than the glass sheets and then cut to size after sandwiched between the glass sheets by cutting off its end portion protruding from the glass sheets. After that, the glass sheet and interlayer assembly is processed by tacking rolls for initial adhesion and then by an autoclave for permanent fastening.

In order to cut off the protruding end portion of the interlayer, it has been practiced to first locate the glass sheet and interlayer assembly in place, i.e., in a predetermined base position by means of locating tools adapted for abutment upon the corresponding edges of one of the glass sheets which are nearly rectangular and then cut off the protruding end portion of the interlayer by means of a cutter adapted to move along a predetermined path which is fixedly set on the basis of the base position of the assembly.

With the prior art cutting apparatus, cutting of the protruding end portion of the interlayer is carried out without detecting the edges of the glass sheets and thereby knowing whether the glass sheet and interlayer assembly is located in place.

A problem of the prior apparatus is that the protruding end portion of the interlayer may possibly be turned up and sandwiched between some locating tool or tools and the corresponding edge or edges of the glass sheet, causing the assembly to be largely moved out of place, i.e., out of the base position and therefore variations in cutting off of the interlayer and, in some cases, causing damage of the cutter and the edges of the glass sheets.

SUMMARY OF THE INVENTION

In accordance with the present invention, there is provided a device for detecting an edge of a transparent sheet of a laminated transparent and translucent sheet assembly, which comprises a light source disposed on one side of the laminated sheet assembly for throwing light toward an edge portion of the laminated sheet assembly and thereby producing a shadow of an edge of the transparent sheet on a translucent sheet of the laminated sheet assembly, a photosensor disposed on the other side of the laminated sheet assembly for detecting intensity of light transmitted through the edge portion of the laminated sheet assembly and producing an electrical output which varies depending upon a variation of intensity of light supplied thereto, lens means for forming a clear image of the shadow on the photosensor, and picture processing means for determining the location of the edge of the transparent sheet on the basis of a change of the electrical output of the photosensor.

In accordance with the present invention, there is also provided an apparatus for cutting off a protruding edge of an interlayer sandwiched between two glass sheets, which comprises means for optically detecting edges of the glass sheets and producing signals representative thereof, means for computing an amount of movement of the glass sheets out of a predetermined base position thereof in response to signals from said detecting means and producing a signal representative thereof, and means for cutting off the protruding end portion of the interlayer through adjustment in position in response to the signal from the computing means.

The above device makes it possible to detect an edge of a transparent sheet of a laminated sheet assembly of the described kind accurately and assuredly. Further, the above apparatus is effective for overcoming the above noted problems inherent in the prior art.

It is accordingly an object of the present invention to provide a device for detecting an edge of a transparent sheet of a laminated transparent and translucent sheet assembly, which is accurate and reliable in operation.

It is another object of the present invention to provide a device of the above described character which is useful for detecting relative movement of laminated transparent sheets and thereby knowing whether the laminated sheet assembly is defective.

It is a further object of the present invention to provide an apparatus for cutting off a protruding edge of an interlayer sandwiched between two glass sheets, which is accurate and reliable in operation.

It is a further object of the present invention to provide an apparatus of the above described character which can prevent damages of a cutting tool and of edges of glass sheets assuredly.

BRIEF DESCRIPTION OF THE DRAWINGS

FIG. 3 is a cartesian coordinate system used for computing movement of a glass sheet and interlayer assembly out of its base position in the apparatus of

DESCRIPTION OF THE PREFERRED EMBODIMENTS

Figure 1:
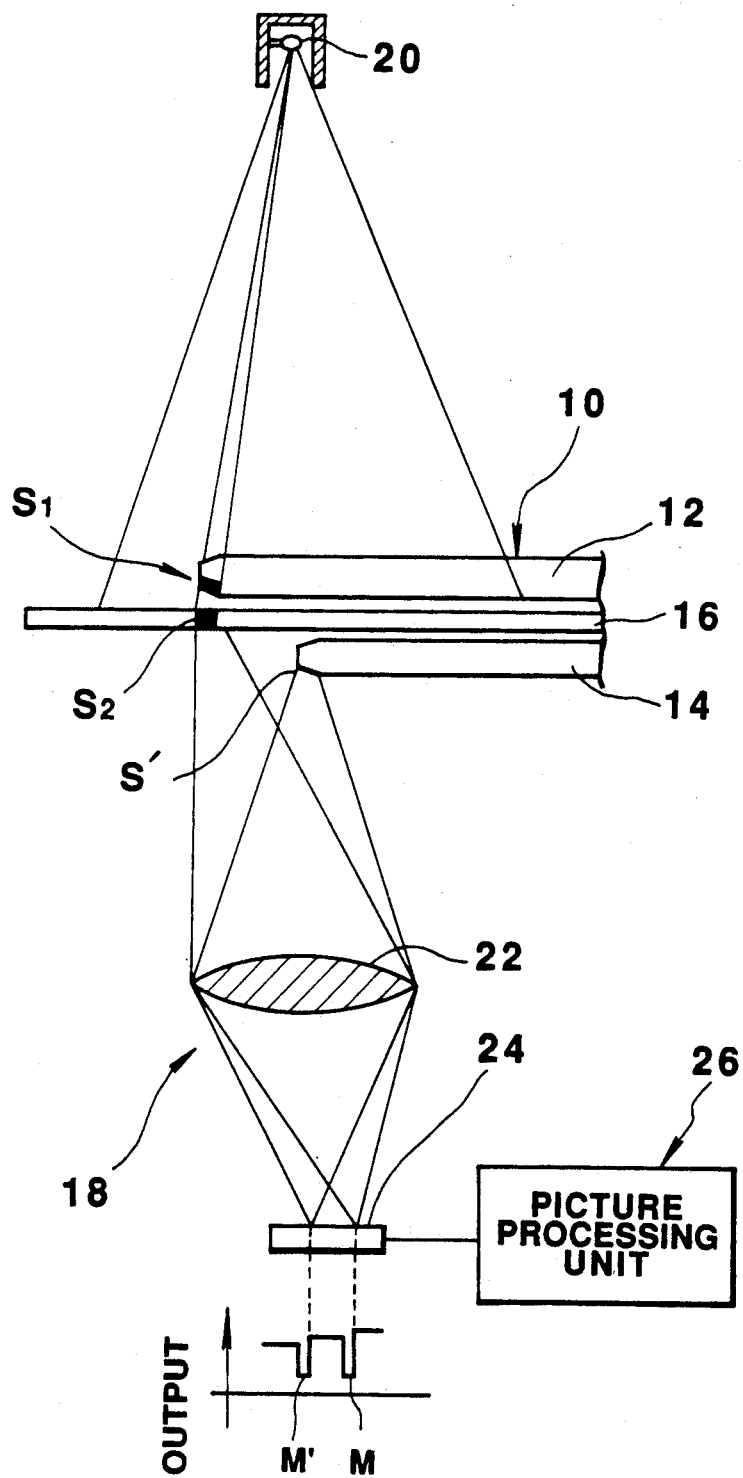
FIG. 1 is a device for detecting an edge of a transparent sheet of a laminated transparent and translucent sheet assembly according to an embodiment of the present invention.

Referring first to FIG. 1, a laminated sheet assembly 10 consists of nearly rectangular transparent sheets 12, 14 as glass sheets for a laminated safety glass, etc. and a translucent interlayer 16 as an interlayer of polyvinyl butyral or the like prior to being processed by an autoclave, which is sandwiched between the transparent sheets 12, 14 and bonded to same.

A device for detecting an edge of the laminated sheet assembly 10 is generally indicated by the reference numeral 18 and includes a light source 20 as a tungsten halogen lamp, a convex lens 22 and a photosensor 24 which are joined to constitute an integral unit as an ITV camera, and a picture processing unit 26. Though not shown, a hood formed with a circular hole of 10 mm in diameter is attached to the ITV camera so as to shut off light disturbance. The light source 20 is disposed at a distance of 1.0 to 2.0 m from the laminated sheet assembly 10, and the ITV camera is at a distance of about 10 cm. An air source may additionally be provided to blow air toward the protruding end portion of the interlayer 16 when the protruding end portion is so large as to bend downwardly and disable edge detection by the device 18.

In operation, the light source 20 throws light toward an edge and its adjacent part of the laminated sheet assembly 10 so that a shade Sl is produced in a beveled or chamferred edge portion, i.e., a so-called seaming portion of the transparent sheet 12, which is one of the transparent sheets nearer to the light source 20, and is cast as a dark image S2 on the translucent sheet 16. On the other hand, since the translucent sheet 16 transmits light though to a certain reduced extent, a shade or dark image S' is produced in a seaming portion of the transparent sheet 14, which is one of the transparent sheets remoter from the light source 20. The images S2 and S' are clearly formed on the photosensor 24 through adjustment of the position of the convex lens 22, i.e., through adjustment of the focus of the ITV camera. Since the photosensor 24 increases its output current with increase of intensity of light supplied thereto, the portions where the output current of the photosensor 24 are reduced extremely are regarded as representing the edges of the transparent sheets 12, 14. That is, by turning on the light source 20 and focusing the ITV camera on the translucent interlayer 16, the edges of the transparent sheets 12, 14 are represented by the two extremely small output portions M, M' of the photosensor 24. By processing the output of the o photosensor 24 by the picture processing unit 26, the edges of the transparent sheets 12, 14, i.e., an edge of the laminated sheet assembly 10 can be detected.

In the above, it will be noted that with the edge detecting device 18 not only the edge of the transparent sheet 12 nearer to the light source 20 but the edge of the transparent sheet 14 remoter from the light source 20 can be detected. Accordingly, with the edge detecting device 18 relative movement between the transparent sheets 12, 14 can be detected to know whether the relative movement is within an allowable range.

It is further to be noted that while it is desirable for the transparent sheet to be provided with a so-called seaming edge (i.e., a beveled or chamferred edge), the similar detection of the edge of the transparent sheet can be attained by making the light from the light source 20 be incident on the edge of the transparent sheet at a predetermined angle so that the shadow of the edge which is perpendicular to the opposed surfaces of the transparent sheet, is cast on the interlayer 16 even if the transparent sheet is not provided with a seaming edge.

Figure 2:
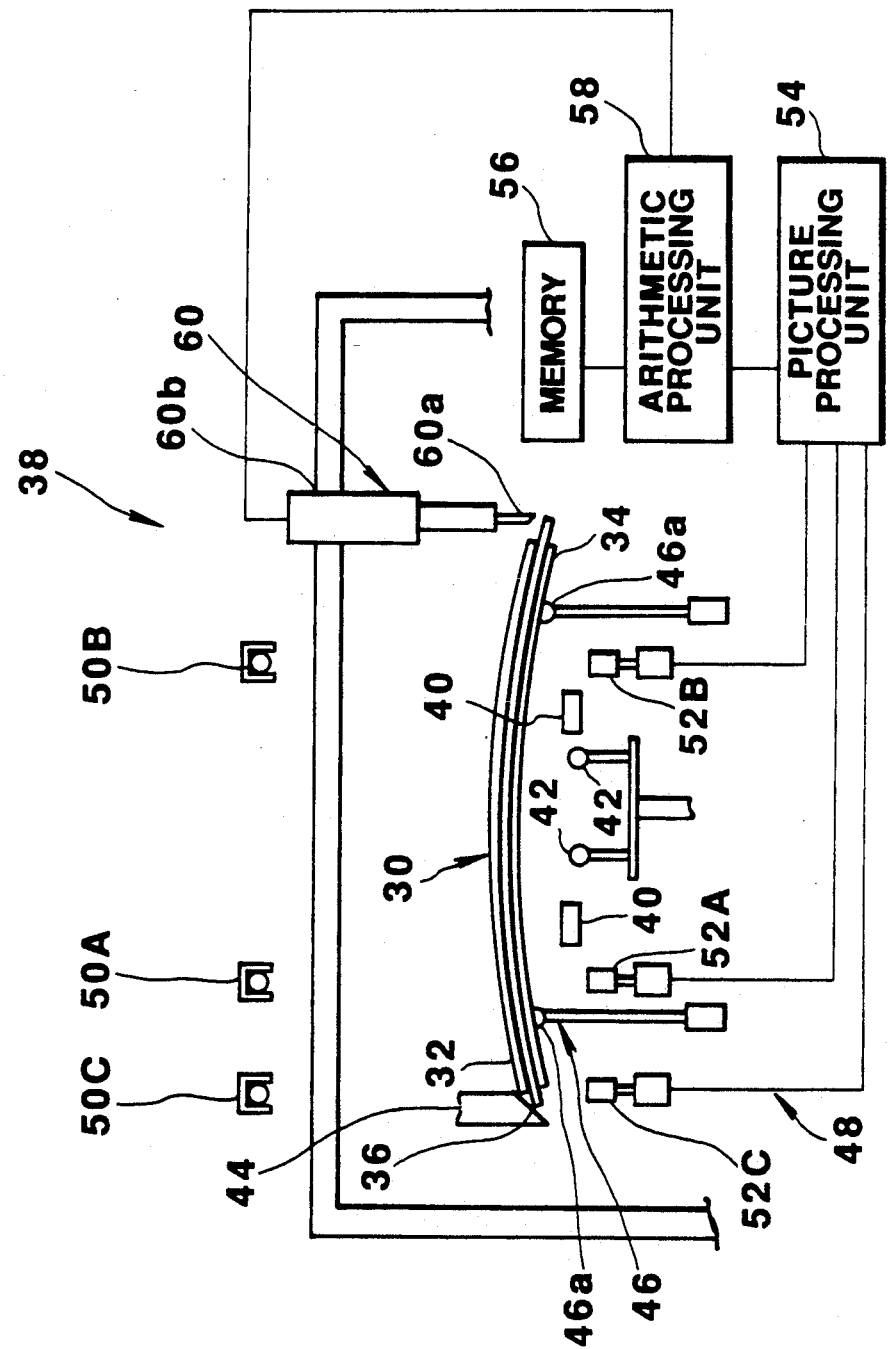
FIG. 2 is a schematic elevational view of an apparatus, which incorporates therein the device of FIG. 1, for cutting a protruding edge of an interlayer sandwiched between two glass sheets.
Figure 3:
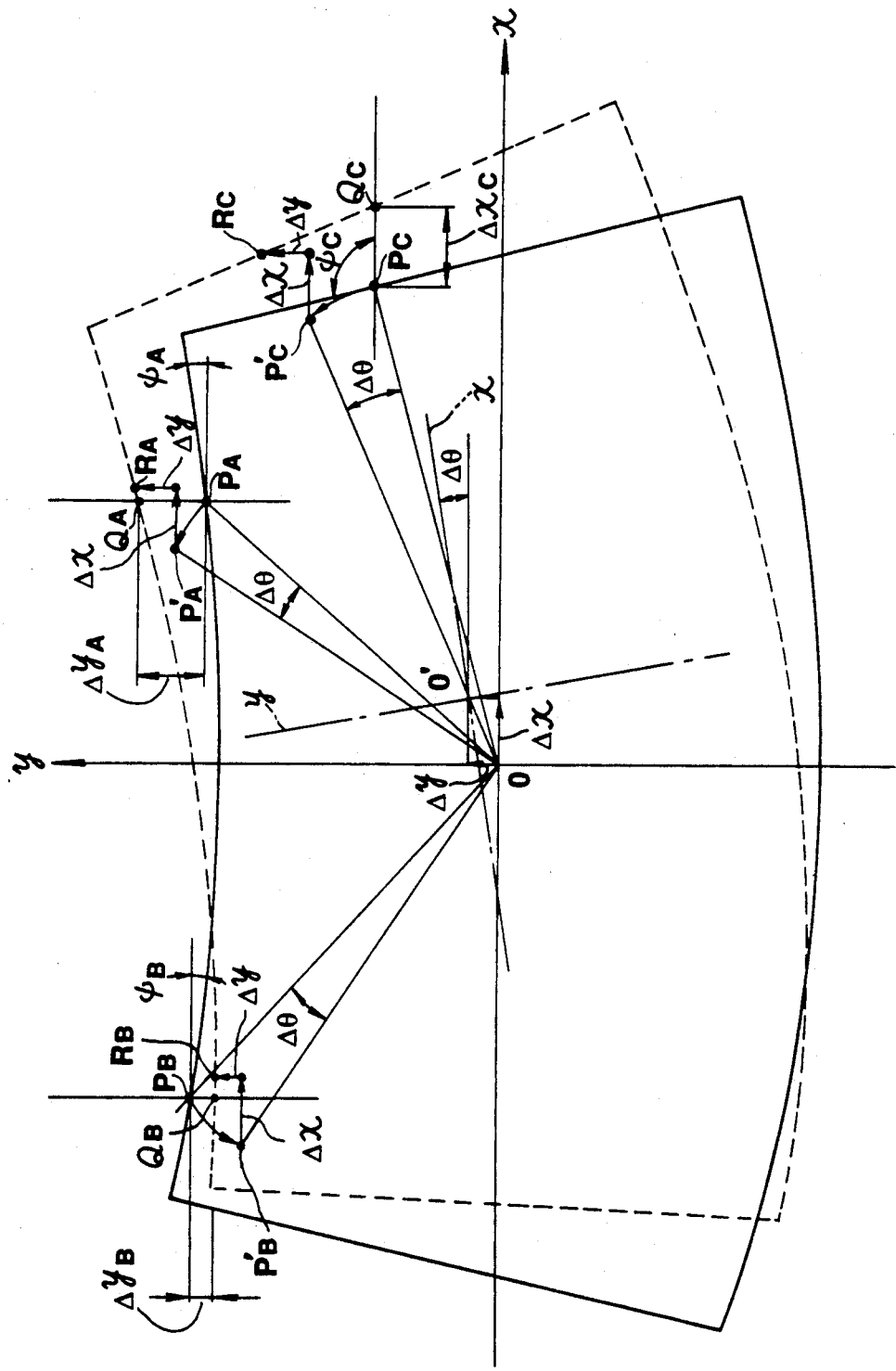

Referring to FIGS. 2 and 3, a glass sheet and interlayer assembly is generally indicated by the reference numeral 30 and consists of nearly rectangular transparent glass sheets 32, 34 and an interlayer 36 of polyvinyl butyral or the like, sandwiched between the glass sheets 32, 34 and bonded to same. The assembly is in the state prior to being processed by tacking rolls for initial adhesion. The interlayer 36 is so sized as to protrude 50 to 100 mm from the respective edges of the glass sheets 32, 34.

The protruding end portion of the interlayer 36 is cut off in the following manner by means of an apparatus 38 of this invention.

The glass sheet and interlayer assembly 30 is conveyed by a belt conveyor 40 to vertically movable free rolls 42 where it is elevated by the free rolls 42 and freely movably supported on same above the conveyor 40. Under this condition, a plurality of locating tools 44, though only one is shown, are brought into contact with the corresponding edges of the glass sheet and interlayer assembly 30 for thereby roughly locating the assembly 30 in place, i.e., locating the assembly 30 adjacent a predetermined base position. A suction cup unit 46 having a plurality of suction cups 46a is moved upwardly so as to support the assembly 30 in the located position, while on the other hand the
locating tools 44 and the free rolls 42 are returned to their rest positions.

Under the condition where the glass sheet and interlayer assembly 30 is stationarily supported by the suction cup unit 46, detection of the edges of the laminated glass sheets 32, 34 and computation of the amount of movement of the assembly 30 out of the base position are performed in the following manner.

The detection of the edges of the glass sheets 32, 34 is performed by an edge detecting device 48 including three sets of light sources 50A, 50B, 50C and ITV cameras 52A, 52B, 52C, and a picture processing unit 54.

While the interlayer 36 at this production process is translucent, the shadows of seaming portions of the glass sheet 32 are cast on the surface of the interlayer 36. By focusing the ITV cameras 52A, 52B, 52C on the shadows, the edges of the glass sheet 32 can o be detected.

In this connection, a plane cartesian coordinate system shown in FIG. 3 is used for computing the amount of movement of the assembly 30 out of place, i.e., of a predetermined base position.

In the plane coordinate system in FIG. 3, the laminated glass sheets 32, 34 of the assembly 30 accurately located in place, i.e., located in a predetermined base position is depicted by the solid line. The ITV cameras 52A, 52B, 52C have windows elongated in parallel to the y-axis, y-axis and x-axis, respectively and are disposed so that their base positions are $P_A(x_A, y_A)$. $P_B(x_B, y_B)$, $P_C(x_C, y_C)$, respectively. The base positions $P_A$, $P_B$, $P_C$ of the ITV cameras 52A, 52B, 52C are stored in a memory 56 together with the angles $\psi_A$, $\psi_B$, $\psi_C$. The angles $\psi_A$, $\psi_B$, $\psi_C$ respectively indicate inclinations of the peripheral portions adjacent to the points $P_A$, $P_B$, $P_C$ with respect to the x-axis, x-axis, y-axis when the peripheral portions adjacent to the points P4, P8, Pc are approximated to straight lines.

In this instance, assuming that the movement of the assembly 30 from the solid line position to the dotted line position causes the points $P_A$, $P_B$, $P_c$ to be moved into $R_A$, $R_B$, $R_c$, respectively, the edges of the thus moved assembly 30 are detected by the ITV cameras 52A, 52B, 52C. On the basis of this detection, the coordinates of the points $P_A(x_A, y_A)$. $P_B(x_B, y_B)$. $P_C(x_c, y_c)$ are translated into the coordinates of $Q_A(X_A, y'_A)$, $Q_B(X_B, y'_{BB})$ $Q_C(X'_C, y_c)$ by means of the picture processing unit 54, respectively and the apparent movements $\Delta Y_A$, $\Delta Y_B$, $\Delta X_c$ at the ITV cameras 52A, 52B, 52C are computed from $y'_A - Y_A$, $y'_B - Y_B$, $x'_C - x_c$ by means of an arithmetic processing unit 58, respectively.

On the other hand, true movement of the glass sheet and interlayer assembly 30 represented by movement of the points from $P_A$, $P_B$, $P_C$ to $R_A$, $R_B$, $R_C$ is expressed by the angle of rotation $\Delta\theta$ and parallel movements $\Delta x$, $\Delta y$. That is, in response to the movement of the assembly 30, the point $P_A$ is moved into the point $P'_a$ through turning of an angle $\Delta\theta$ about the origin 0 and with a distance 0-PA for a radius. The o coordinates of the point $P'_A$ can be approximated to $x_A - Y_A \cdot \Delta\theta$, $Y_A + x_A \cdot \Delta\theta$) since the true movement is actually quite small, and the coordinates of the point $R_A$ is expressed by $(x_A + \Delta x - y_A \cdot \Delta\theta, y_A + \Delta y + x_A \cdot \Delta\theta)$, by the arithmetic processing unit 58.

In this instance, since $\Delta\theta$, $\Delta x$, $\Delta y$ are actually quite small, a peripheral portion of the assembly 30 adjacent to the point $R_a$ can be approximated to a straight line, and the inclination of the straight line $Q_A - R_A$ can be approximated to $\tan\psi_A$, the following relational expression is obtained.

$$\tan\psi_A = \{(Y_A + \Delta y_a) - (y_a + \Delta y + x_A \cdot \Delta\theta)\}\{x_A - (x_A + \Delta x - Y_A \cdot \Delta\theta)\}, \text{ that is,}$$

$$\Delta Y_A = -\tan\psi_A \cdot \Delta x + \Delta y + (x_A + y_A \tan\psi A) \cdot \Delta\theta \quad (1)$$

Then, from the movement of the point $P_B$ to the point R8. The following relational expression is obtained.

$$\Delta y_B = -\tan\psi_B \cdot \Delta x + \Delta y + (x_B + y_B \tan\psi B) \cdot \Delta\theta \quad (2)$$

From the movement of the point P to the point R, the following relational expression is obtained.

$$\Delta y_c = \Delta x - \frac{1}{\tan\psi_c} \cdot \Delta y - \left(\frac{x_c}{\tan\psi_c} + y_c\right) \cdot \Delta\theta \quad (3)$$

From the relational expressions (1), (2), (3), the true movements $\Delta x$ $\Delta y$, $\Delta\theta$ are obtained by the operation of the arithmetic processing unit 11.

A cutter unit 60 consists of a cutter 60a and a carrier 60b as a robot, and is movable so as to offset movement of the assembly 30 out of the base position in response to signals representative of the movement $\Delta x$, $\Delta y$, $\Delta\theta$ and supplied to the carrier 60b from the arithmetic processing unit 58 and thereby be capable of accurately cutting the protruded end portion of the interlayer 30 to a predetermined size, i.e., to such a size that the amount of protrusion on the short edge side of the assembly 1 is within the range from 0.5 to 1.0 mm and on the long edge side within the range from 1 to 10 mm.

Thereafter, the glass sheet and interlayer assembly 30 is processed by tacking rolls for initial adhesion and by an autoclave for permanent fastening, whereby to be formed into a laminated safety glass.

What is claimed is:

1. An apparatus for cutting off a protruding edge of a translucent sheet laminated to a transparent sheet in a laminated translucent and transparent sheet assembly, comprising:
   means for holding the assembly approximately fixed relative to said holding means and for holding the assembly approximately adjacent to a reference position;
   means for optically detecting a position of an edge of the transparent sheet relative to the reference position and producing signals representative thereof;
   means for computing an amount of movement of the assembly out of the reference position depending upon the signals from said detecting means and for producing a signal representative thereof; and
   means for cutting off the protruding end portion of the translucent sheet of the translucent and transparent sheet assembly while adjusting a position of the cutting means relative to the reference position depending on the signal from said comprising means for compensating for the amount of movement of the assembly out of the reference position.

2. The apparatus of claim 6, wherein said detecting means include:
   a light source disposed on one side of the laminated sheet assembly for throwing light toward an edge portion of the laminated sheet assembly and thereby producing a shadow of an edge of the transparent sheet on a translucent sheet of the laminated sheet assembly;
   a photosensor disposed on the other side of the laminated sheet assembly for detecting intensity of light transmitted through the edge portion of the laminated sheet assembly and producing an electrical output which varies depending upon variation of intensity of light supplied thereto;
   lens means for forming a clear image of the shadow of said photosensor; and
   picture processing means for determining the location of the edge of the transparent sheet on the basis of a variation of the electrical output of said photosensor.

3. The apparatus as claimed in claim 2 wherein the edge of the transparent sheet is beveled.

4. The apparatus as claimed in claim 2 wherein the edge of the transparent sheet is perpendicular to opposed surfaces of the transparent sheet, and the light from the light source is incident on the edge of the transparent sheet at a predetermined angle.

5. The apparatus as claimed in claim 2 wherein the laminated sheet assembly further includes another transparent sheet on the side of the translucent sheet opposite to the first mentioned transparent sheet, and said light source is operative to cause a shade in an edge portion of the second mentioned transparent sheet, said lens means being operative to form a clear image of the shade on said photosensor so that said picture processing unit is further operative to determine the position of the edge of the second mentioned transparent sheet.

6. The device as claimed in claim 2 wherein said light source is a tungsten halogen lamp, and said lens means and said photosensor constitute an ITV camera.

7. The apparatus as claimed in claim 1, in which the laminated sheet assembly further includes,
   another transparent sheet,
   and wherein:
   the transparent sheets are glass sheets; and
   the translucent sheet is a protruding interlayer sandwiched between the glass sheets in a glass sheet and interlayer assembly.

8. The apparatus as claimed in claim 7, which further include:
   means for movably supporting the glass sheet and interlayer assembly;
   means for locating the glass sheet and interlayer assembly, supported by said movably supporting means, approximately adjacent a reference position; and
   means for activating said holding means while the glass sheet and interlayer assembly are approximately adjacent the to the reference position obtained by said locating means;

and in which the holding means are permanently fixed in relation to said detecting means and said reference position.

9. The apparatus as claimed in claim 7, in which the position of an edge of each glass sheet is detected and signaled.

10. The apparatus as claimed in claim 7 wherein said cutting means comprises a cutter, and a carrier carrying said cutter and movable along said the edges of the glass sheets, said carrier being operative to change its path which it follows upon movement along the edges of the glass sheets, in such a way as to offset the movement of the glass sheets out of the reference position in response to said signal from said computing means.

11. The apparatus as claimed in claim 7 wherein said detecting means comprises a plurality of photosensors for detecting apparent movements of the edges of the glass sheets on the presumption that movement of the glass sheets out of place causes predetermined points on the edges of the glass sheets to move in parallel to corresponding axes of a predetermined cartesian coordinate system, and said computing means comprises an arithmetic processing unit for obtaining true movements of the edges of the glass sheets on the basis of said apparent movements.

12. A device for detecting an edge of a transparent sheet of a laminated transparent and translucent sheet assembly, comprising:

a light source disposed on one side of the laminated sheet assembly for throwing light toward an edge portion of the laminated sheet assembly and thereby producing a shadow of an edge of the transparent sheet on a translucent sheet of the laminated sheet assembly;

a photosensor disposed on the other side of the laminated sheet assembly for detecting intensity of light transmitted through the edge portion of the laminated sheet assembly and producing an electrical output which varies depending upon variation of intensity of light supplied thereto;

leans means for forming a clear image of the shadow of said photosensor; and picture processing means for determining the location of the edge of the transparent sheet on the basis of a variation of the electrical output of said photosensor.

* * * * *